United States Patent
Zamora (10) Patent No.: US 10,405,956 B1
(45) Date of Patent: Sep. 10, 2019

(54) DEVICE TO ADMINISTER A SOLID ANIMAL MEDICINE TO AN ANIMAL

(71) Applicant: Robert Zamora, Torrance, CA (US)

(72) Inventor: Robert Zamora, Torrance, CA (US)

( * ) Notice: Subject to any disclaimer, the term of this patent is extended or adjusted under 35 U.S.C. 154(b) by 199 days.

(21) Appl. No.: 15/683,688

(22) Filed: Aug. 22, 2017

Related U.S. Application Data (62) Division of application No. 14/221,050, filed on Mar. 20, 2014, now Pat. No. 9,775,696.

(51) Int. Cl.
*A61D 7/00* (2006.01)
*A61M 31/00* (2006.01)
*A61M 37/00* (2006.01)

(52) U.S. Cl.
CPC ............. *A61D 7/00* (2013.01); *A61M 31/007* (2013.01); *A61M 37/0069* (2013.01); *A61M 31/00* (2013.01)

(58) Field of Classification Search
CPC .. A61M 37/0069; A61M 2250/00; A61D 7/00
USPC .......................................................... 604/61
See application file for complete search history.

(56) References Cited

U.S. PATENT DOCUMENTS

| | | | |
|---|---|---|---|
| 3,241,541 A * | 3/1966 | Coffey, Sr. ............... | F41B 7/006 124/27 |
| 3,830,500 A * | 8/1974 | Ventura .................. | A63B 65/12 124/10 |
| 3,888,258 A * | 6/1975 | Akiyama ............... | A61F 11/002 128/DIG. 8 |
| 3,936,052 A * | 2/1976 | Hornsby, Jr. ............. | A63F 9/02 273/357 |
| 4,060,083 A | 11/1977 | Hanson | |
| 4,735,594 A * | 4/1988 | Miller ...................... | G07D 1/08 124/50 |
| 5,578,004 A | 11/1996 | Liang | |
| 5,681,279 A | 10/1997 | Roper et al. | |
| 6,763,971 B1 * | 7/2004 | Tong ........................ | G07F 11/44 221/151 |
| 6,960,183 B2 | 11/2005 | Nicolette | |
| 7,118,550 B2 * | 10/2006 | Loomis ................... | A61F 13/26 604/60 |
| 7,703,447 B2 * | 4/2010 | Caveza ................ | A01K 15/026 119/51.01 |
| 7,744,558 B2 | 6/2010 | Maag | |
| 8,062,248 B2 | 11/2011 | Kindel | |

* cited by examiner

*Primary Examiner* — William R Carpenter (74) *Attorney, Agent, or Firm* — Thomas I. Rozsa (57) ABSTRACT

A device to administer multiple capsules or pills or a combination of capsules or pills into the mouth of an animal. The device is gravity fed and is composed of seven parts. The parts are: (i) a molded tee handle, (ii) a molded trigger pin (tee handle), (iii) a spring pin (trigger release pin) which is part of the molded trigger; (iv) a torsion spring; (v) a tube which can be 6 inches long with an outer diameter such as ½ inch with varying inner diameters resulting from different interior thicknesses of the barrel; (vi) a ⅜ inch ID#4 pan head screw; and (vii) a ⅞ inch diameter disc.

5 Claims, 7 Drawing Sheets

DEVICE TO ADMINISTER A SOLID ANIMAL MEDICINE TO AN ANIMAL

CROSS-REFERENCE TO RELATED APPLICATION

This patent application is a divisional of application Ser. No. 14/221,050 filed on Mar. 20, 2014, now pending.

BACKGROUND OF THE INVENTION

1. Field of the Invention

The present invention relates to the field of handheld solid animal medicine administrator to enable an owner of a pet such as a dog or cat to hold the animal with one hand and cause one or more pills to be inserted into the animal's mouth in a manner where a front portion of the administrator travels past the animal's tongue so that the animal will have to swallow the pills and not spit them out.

2. Description of the Prior Art

In general, devices to administer a pill to an animal are known in the prior art. The following six (6) patents are the closest prior art known to the inventor.

1. U.S. Pat. No. 4,060,083 issued to Hanson on Nov. 29, 1977 for "PILL GUN" which discloses a handheld pill gun for administering medicinal pills and capsules including a plastic barrel and plunger, and rigid broad surface manipulating bars on the barrel and spaced apart to bear firmly against the front and rear surfaces of the person's fingers.

2. U.S. Pat. No. 5,578,004 issued to Liang on Nov. 26, 1996 for "FEED DRUG INJECTOR" which discloses a feed drug injector comprising a nipple device, a nipple plug inserted in the nipple device, a front end of a cylinder inserted in the nipple plug, and a push rod inserted in the cylinder. The nipple device has a base and a nipple head. Two inner recesses are formed on the inner periphery of the base. A passage is formed in the nipple head. A Y-shaped hole is formed in the front of the passage. A bevel is formed on the front surface of the nipple head. Three apertures which are formed on the bevel and two front sides of the nipple head communicate with the Y-shaped hole. The nipple plug has a disk with an inner thread, a Y-shaped bar, and three circular holes formed on the disk. Two protrusions are disposed on the outer periphery of the disk. The protrusion engages with the inner recess.

3. U.S. Pat. No. 5,681,279 issued to Roper et al. on Oct. 28, 1997 for "PILL DISPENSING SYRINGE" which discloses a pill dispensing syringe comprising a cylindrical outer housing, a water injection cylinder slidably mounted within the interior bore of the outer housing, a piston slidably mounted within the interior bore of the water injection cylinder, a piston rod fixedly attached to the piston and extending therefrom through the interior bores of the water injection cylinder and the outer housing, a cylindrical pill dispensing sleeve fixedly attached to the opposing end of the outer housing, the opposing end of the pill dispensing sleeve being adapted for holding a pill, and a cylindrical water injection tube slidably mounted within the interior bore of the pill dispensing sleeve, and end of the water injection tube being fixedly attached to the water injection cylinder.

4. U.S. Pat. No. 6,960,183 issued to Nicolette on Nov. 1, 2005 for "VETERINARY PILL AND CAPSULE DELIVERY DEVICE" which discloses a veterinary pill/capsule delivery device comprised of a dispensing head for holding a pill the or capsule, the dispensing head being attached to the end of a syringe component for ejecting the pill or capsule out from the dispensing head into the animal's mouth while at the same time injecting a quantity of water into the mouth. The syringe component includes a push-rod that protrudes into the dispensing head for ejecting the pill/capsule therefrom, plus water release holes near the dispensing head for simultaneously jetting water out of the syringe component into the animal's mouth, thereby compelling the animal to swallow the pill.

5. U.S. Pat. No. 7,744,558 issued to Maag on Jun. 29, 2010 for "PILL PLUNGER" which discloses a pill plunger including a hollow tube having a forward end and a rearward end. A rod or plunger has a forward end having a dished out portion for receiving medication and a rearward end having a button. The plunger occupies the tube with the dished out portion at the forward end of the tube and the button extending from the rearward end of the tube. medication is placed in the dished out portion, when is then retracted into the tube. After insertion of the tube into a patient's mouth, the button is depressed to extend the plunger and dispense the medication. A spring can be used to retract the plunger upon release of the button. The dished out portion can be sealed to carry a fluid or powder. A dual dished out portion can be provided in the rod, and a window can be formed in the hollow tube.

6. U.S. Pat. No. 8,062,248 issued to Kindel on Nov. 22, 2011 which discloses a pill dispenser including a housing having front, rear and side walls defining a hollow interior. A pill holding member is removably coupled to the housing front wall and defines a frontward bore configured to receive a pill and being in operative communication with the housing front opening. An elongate plunger shaft having proximal and distal ends is positioned and extends through the housing. The shaft is movable between a retracted configuration in which the distal end extends from the housing rear wall and an actuated configuration in which the distal end is adjacent the housing rear wall. A spring is positioned in the dispenser housing and operatively connected to the plunger shaft for selectively moving the plunger shaft between the retracted and actuated configurations so as to eject a pill from the holding member. The shaft may be retracted to selected positions before being spring actuated to dispense a pill.

There is a significant need for an improved animal solid animal medicine administrator that can safely administer more than one pill or capsule.

SUMMARY OF THE INVENTION

The present invention is a device to administer multiple capsules or pills or a combination of capsules or pills into the mouth of an animal. The device is gravity fed and is composed of seven parts. The parts are: (i) a molded tee handle, (ii) a molded trigger pin (tee handle), (iii) a spring pin (trigger release pin) which is part of the molded trigger; (iv) a torsion spring; (v) a tube which can be 6 inches long with an outer diameter such as ½ inch with varying inner diameters resulting from different interior thicknesses of the barrel; (vi) a ⅜ inch ID#4 pan head screw; and (vii) a ⅞ inch diameter disc.

The tee handle and trigger are made using a mold for each part. After the mold is ready, two bores in the handle are made, along with a notch where the trigger mounts. Two holes are also drilled—one to mount the trigger and spring assembly, which include the trigger for the release pin and one for the disc assembly. A hole is also drilled in the tube to allow the release pin to pass through the tube. There is also a notch created on the trigger and an alignment mark for when the tube is removed for cleaning. The trigger has one spring pin with a release pin as part of the trigger mold used as the pill/capsule release. The tee handle, trigger and flat spring are put together using one of the spring pins. The 7/8 inch disc is attached using the #4 pan head screw. After the tube is inserted into the handle where the tube is aligned with the alignment mark, the device to administer a solid animal medicine to an animal is assembled and ready to use. The solid animal medicine is selected from the group consisting of pills and capsules.

By turning the disc on the end to expose the bore where the solid animal medicine selected from the group consisting of pills and capsules are added, the disc is then closed. When the pet's mouth is opened. the tube is inserted into the pet's mouth and the solid animal medicine is released into the pet's mouth.

The solid animal medicine administrator is gravity fed. There is a chamber that is opened and in which the solid animal medicine pills are placed so they fall into the dispensing tube which can be any shape in addition to cylindrical and is more broadly defined as "dispensing member", that goes past the animal's tongue and into the animal's throat. There are different-sized barrels for the gun depending upon the size of the pill so it does not get stuck if the barrel is too small. The barrel itself has a hole in it and there is a blocking member which is also called a blocking pin and that is physically attached to a horizontal portion of a trigger mechanism which in more general terms, is called a release mechanism, and a blocking member. The trigger or the release mechanism is pulled to activate it. Variations on the release mechanism are within the spirit and scope of the present invention.

The present invention has interchangeable barrels and the bulk of the gun is the same. To operate the present invention, the user grabs the lower jaw of the animal and since animals tend to pull back, this allows the tube from the solid medicine animal administrator to be inserted, at the same time using the pet administrator to control the upper part of the animal's jaw. The user does not allow the animal to close its mouth and keeps his/her fingers clear from the animal's teeth. The user holds the solid medicine animal administrator in the opposite hand and then activates the solid medicine animal administrator to cause the pill to go down the animal's throat.

There are three interchangeable tubes wherein the outer diameters are the same size so the trigger mechanism does not need to be changed. The only difference between them is that the thickness of the walls varies wherein the inner diameter is larger or smaller to accommodate different sized pills and the trigger mechanism with the blocking member that prevents the solid animal medicinal from coming down until the trigger is pulled by about 15 degrees which moves the pin out of the way so the pills and capsules can fall down and be forced into the animal's throat.

In an alternative embodiment of the present invention, the tube does not stop at the beginning or the front end of the transverse member of the handle but instead, extends all the way through the entire distance of the transverse member and stops at the location where there is the opening. In this way it is not necessary to change a storage facility in the handle, thereby reducing the cost so there is just one of a given length and the tube of a given length extends through the entire diameter of the transverse member and then extends outwardly so pills can be dispensed.

The present invention addresses the issue of having tubes of different diameters to accommodate larger and smaller pills by making the opening where the tube goes through the entire transverse section of the handle have the largest diameter and then within that tube having smaller tubes with smaller diameters inserted to accommodate pills having different diameters. In this way, the largest diameter is the one that goes all the way through and out of the entire transverse section of the handle and if it is desired to reduce the inner diameter to accommodate smaller pills, it will still have the same outer diameter regardless. It is just that the interior wall of the tube will be thicker to accommodate smaller diameters. There are a multiplicity of tubes, all having the same outer diameter, but the walls have different thicknesses so the inner diameter is smaller, with the thinner outer diameter accommodating the larger tubes and the smallest inner diameter accommodating the smaller tubes.

In another alternative embodiment of the present invention, there is one tube of a given diameter which fits inside the hand piece and then smaller tubes that are inserted within that tube that reduce the interior diameter.

It is also within the spirit and scope of the present invention to have a variation of the present invention where there is a tube of a given outer diameter and that will be replaced with other tubes of the same outer diameter with different inner diameters. Alternatively, there can be one tube that has the largest outer diameter and the largest inner diameter and inserts that go into that tube that reduce the diameter. The smallest practical tube length is 8 inches in diameter and the largest is 16 inches in diameter for each variation. As explained above, while the device is described as a tube, the dispensing part can also be any shape in addition to cylindrical and therefore, can be more broadly described as "dispensing member" to cover any shape in addition to cylindrical.

In order to have variations on the tube, the length can also vary. The invention is strong enough to prevent a large animal from pulling the tube out and choking on it.

In addition, the blocking pin is a separate section or alternatively, the blocking pin is molded into the body of the trigger.

It is preferred to have the angle of the blocking pin bent. The angle can be 90 degrees to the trigger but it can also be as much as 60 degrees so there is a 30 degree range for the pin which will be molded into the trigger.

The torsion spring which is also referred to as a "spring member" is held in place by the round gaps in the back of the trigger and it extends along one way on the horizontal plane and in the space in the handle so that essentially, force of the finger is needed to overcome the force of the spring and then the torsion spring snaps it back into place after the trigger release has been pulled.

The length of the tube from where it exits the transverse retaining member has to be 4 inches on one end and 8 inches for a bigger dog. For a cat it can be 3 inches and for a dog it can be 3 inches to 8 inches. The opening where the medicine which can be a pill or a capsule is rotated into place. The opening generally will not be bigger than 7/8 inch. The inner diameter for the rod has to be at least 7/8 inch but it has to be as large as that opening. The tube generally has an outer diameter of 1/2 inch and the largest practical inner diameter is 3/8 inch or smaller.

The retaining cap is rotatably attached. There can also be a plug and there can also be other methods for sealing it.

The solid animal medicine (selected from the group consisting of pills and capsules) 1 administrator has at least one opening with a solid cylinder where the tube goes all the way through the transverse handle. Another option is that instead of having a solid handle, the handle itself has an opening cylinder which is simply a retaining member to retain the pills. A variation is to have a chamber in the handle as a retainer for the solid animal medicine.

The object of the present invention is to provide an animal medicine administrator which has all of the features and variations as described above.

Defined in detail, the present invention is a device to administer a solid animal medicine to an animal, comprising: (a) a handle having a hand grip section and a transverse section, the transverse section of the handle includes an elongated opening having a given diameter extending from a distal end to a proximal end, the elongated opening of the transverse section of the handle retains a dispensing tube having a distal end aligned with the distal end of the elongated opening in the transverse section, the dispensing tube extends past the proximal end of the elongated opening in the transverse section and extends for a distance of at least several inches to a proximal end of the dispensing tube, the dispensing tube having an exterior wall with an exterior surface having a diameter which enables the dispensing tube to be press fit retained within the elongated opening of the transverse section of the handle, the dispensing tube having an interior hollow chamber surrounded by the dispensing tube exterior wall, the interior hollow chamber having a given interior diameter, the dispensing tube includes a transverse opening located at a given distance from the proximal end of the transverse section of the handle, the transverse opening extending from the exterior surface of the exterior wall into the interior hollow chamber of the dispensing tube; (b) a trigger mechanism rotatably affixed to a proximal opening in the transverse section of the handle, the trigger mechanism including a first section aligned with the dispensing tube and a blocking member which extends through the transverse opening in dispensing tube and into the hollow interior chamber of the dispensing tube, the blocking member extending from an interior surface of the hollow chamber at the transverse opening to adjacent an interior surface of the hollow chamber at a location at an opposite end of the interior diameter of the dispensing tube, the trigger mechanism is affixed to exterior walls of a proximal opening of the hand grip section of the handle with a rotation member supported by a head of the trigger mechanism, the head of the trigger mechanism extends to a trigger section of the trigger mechanism; (c) the hand grip section of the handle having an interior chamber into in which the solid animal medicine selected from the group consisting of pills and capsules are stored with a closing door removably affixed to a bottom wall of the hand grip section; (d) a spring member embedded into the trigger mechanism and partially retained in a slot on an interior surface of a hand grip section and partially retained in a first section of the trigger mechanism; and (e) the distal end of the dispensing tube is closed by a closing member rotatably affixed to a rear wall at the distal end of the transverse section of the handle, the animal medicine inserted into the distal end of the interior chamber of dispensing tube when the closing member is in an open condition, the closing member rotated to a closed position after the solid animal medicine has been inserted into the interior chamber of the dispensing tube, the solid animal medicine travels within the interior chamber of the dispensing tube until further travel is stopped by the blocking member; (f) whereby an animal is restrained and the proximal end of the dispensing tube is inserted into an animal's mouth to adjacent an animal's throat and then a user's hand grips the hand grip section of the handle so that at least one finger of the user's hand applies a squeezing force on the trigger section of the trigger mechanism to move the trigger section toward the interior face of the hand grip section to overcome the force of the spring member to thereby cause the blocking member to rotate out of the interior chamber of the dispensing tube to cause the solid animal medicine to travel to a proximal end of the dispensing tube and out of the proximal end of the interior chamber of the dispensing tube and down the animal's throat and when the squeezing force from the at least one finger is removed, the spring causes the blocking member to rotate back into the hollow chamber of dispensing tube.

Further novel features and other objects of the present invention will become apparent from the following detailed description, discussion and the appended claims, taken in conjunction with the drawings.

BRIEF DESCRIPTION OF THE DRAWINGS

Referring particularly to the drawings for the purpose of illustration only and not limitation, there is illustrated.

DESCRIPTION OF EMBODIMENTS OF THE PRESENT INVENTION

Although specific embodiments of the present invention will now be described with reference to the drawings, it should be understood that such embodiments are by way of example only and merely illustrative of but a small number of the many possible specific embodiments which can represent applications of the principles of the present invention. Various changes and modifications obvious to one skilled in the art to which the present invention pertains are deemed to be within the spirit, scope and contemplation of the present invention as further defined in the appended claims.

Figure 1:
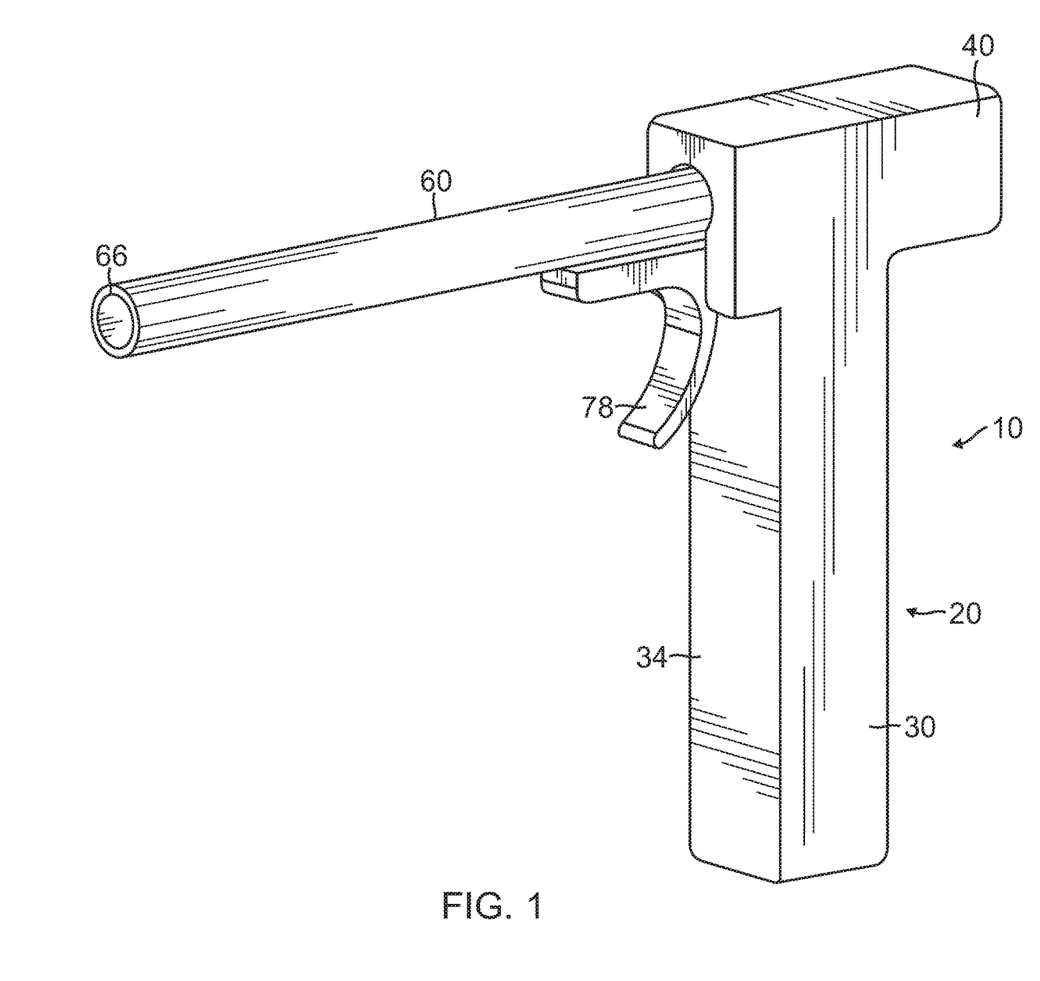
FIG. 1 is a left side perspective view of the present invention solid medicine animal administrator.
Figure 2:
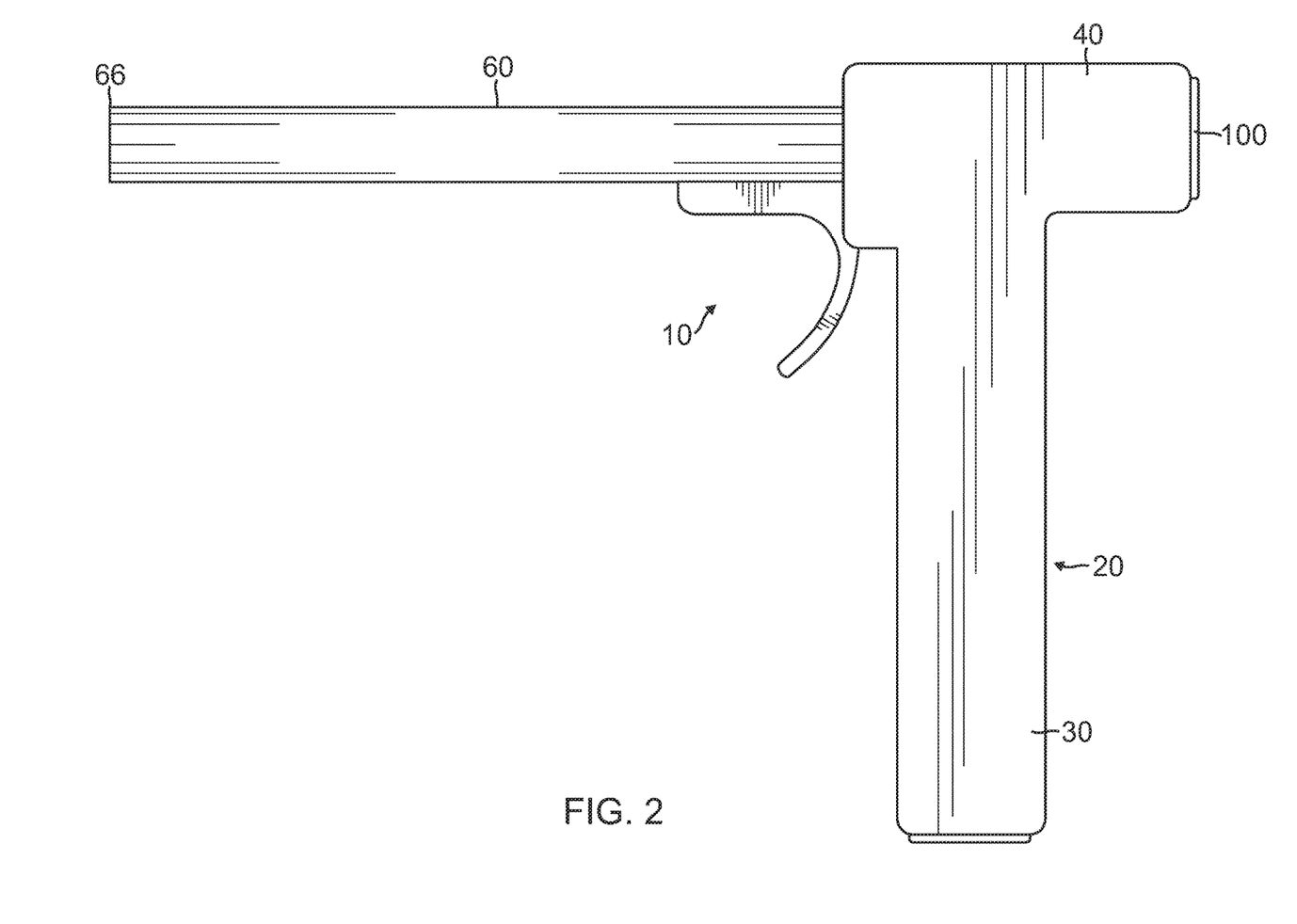
FIG. 2 is a left side elevational view of the present invention solid medicine animal administrator.

Referring to FIGS. 1 and 2, there is illustrated a solid medicine animal administrator 10 of the present invention.

Figure 3:
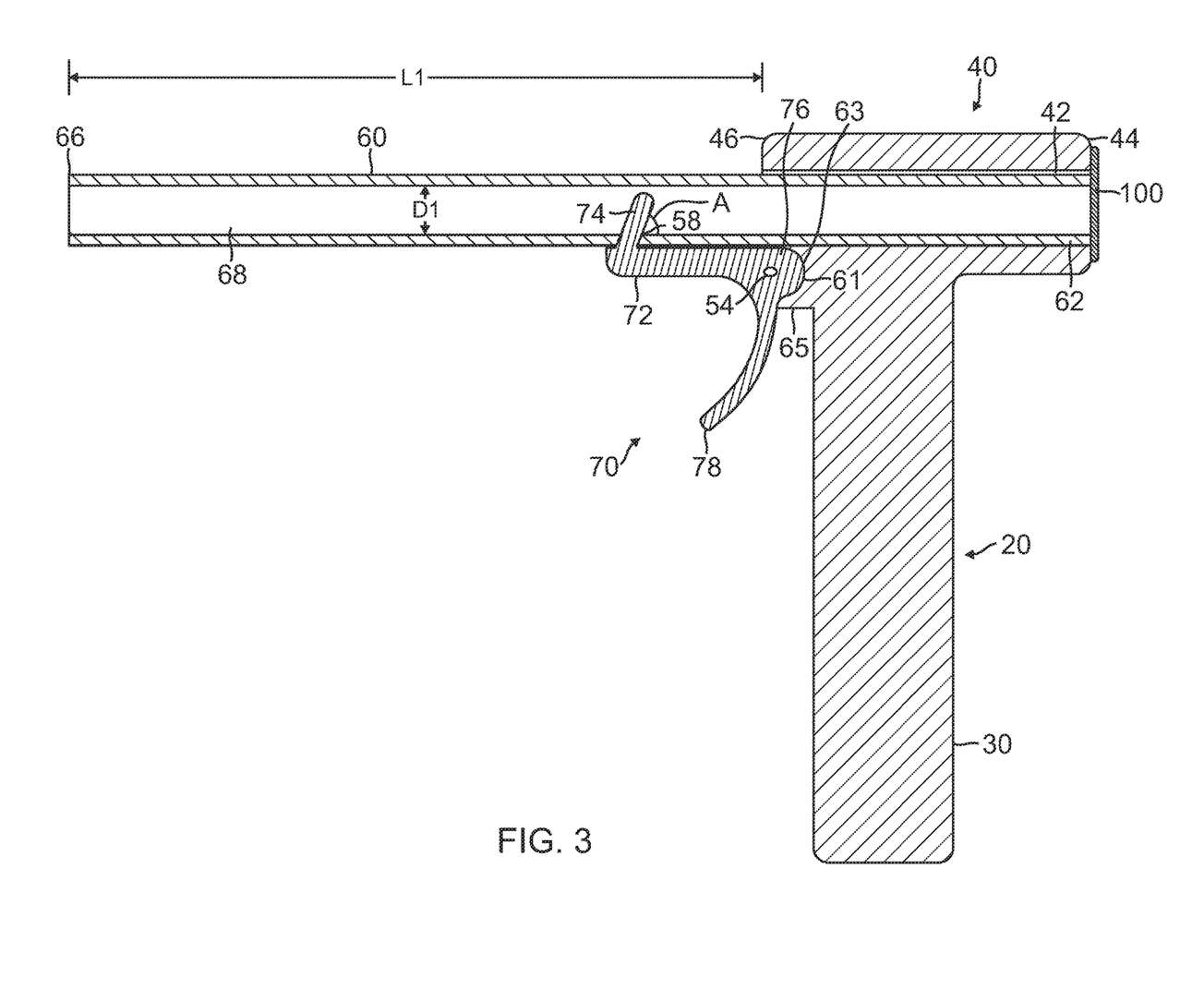
FIG. 3 is a cross sectional view taken along line 3-3 of FIG. 2.

The solid medicine animal administrator 10 includes a handle 20 having a hand grip section 30 and a transverse section 40. Further including the cross-sectional view of FIG. 3, the transverse section 40 has an elongated opening 42 extending from the distal end 44 to the proximal end 46 to receive a dispensing tube 60 having a distal end 62 aligned with the distal end 44 of the opening 42 in the transverse section 40. The dispensing tube 60 extends past the proximal end 46 and transverse section 40 and extends for a distance of at least several inches to its proximal end 66. The dispensing tube 60 includes a transverse opening 68 a given distance "L1" from the proximal end 46 of the transverse section 40 of handle 30.

Referring to FIGS. 3, 5, 6 and 6A, a trigger mechanism 70 is rotatably affixed to a proximal opening 61 in transverse section 60. The trigger 70 has a first section 72 aligned with the dispensing tube 60 and a blocking member 74 which extends through transverse opening 58 in dispensing tube 60 and into the hollow interior chamber 68 of dispensing tube 60. In dispensing tube 60, interior chamber 68 has a diameter "D1". The blocking member 74 extends at an angle "A" between sixty (60) degrees to ninety (90) degrees into chamber 68 and extends for most of diameter "D1". While the interior chamber is described as cylindrical, it will be appreciated that the interior chamber can have any cross-sectional design. Therefore, the blocking member extends from the transverse opening to the remote portion of the internal cylindrical chamber opposite the transverse opening which can be described as the cross-section where the blocking member is almost adjacent the oppositely disposed interior cross-section wall. This principle also applies to the variations described in the paragraphs below with respect to variations in the dispensing tube also more broadly called the "dispensing member". The trigger mechanism 70 is affixed to exterior walls 63 and 65 of proximal opening 61 of handle 60 with a rotation member 54 such as a pin extending through the head 76 of trigger 70 or alternatively, a first outside pin 75 and a second outside pin 77 respectively extending into first open 67 in exterior wall 63 and second opening 69 in exterior wall 65. The head 76 of the trigger mechanism 70 extends to a trigger section 78.

Figure 9:
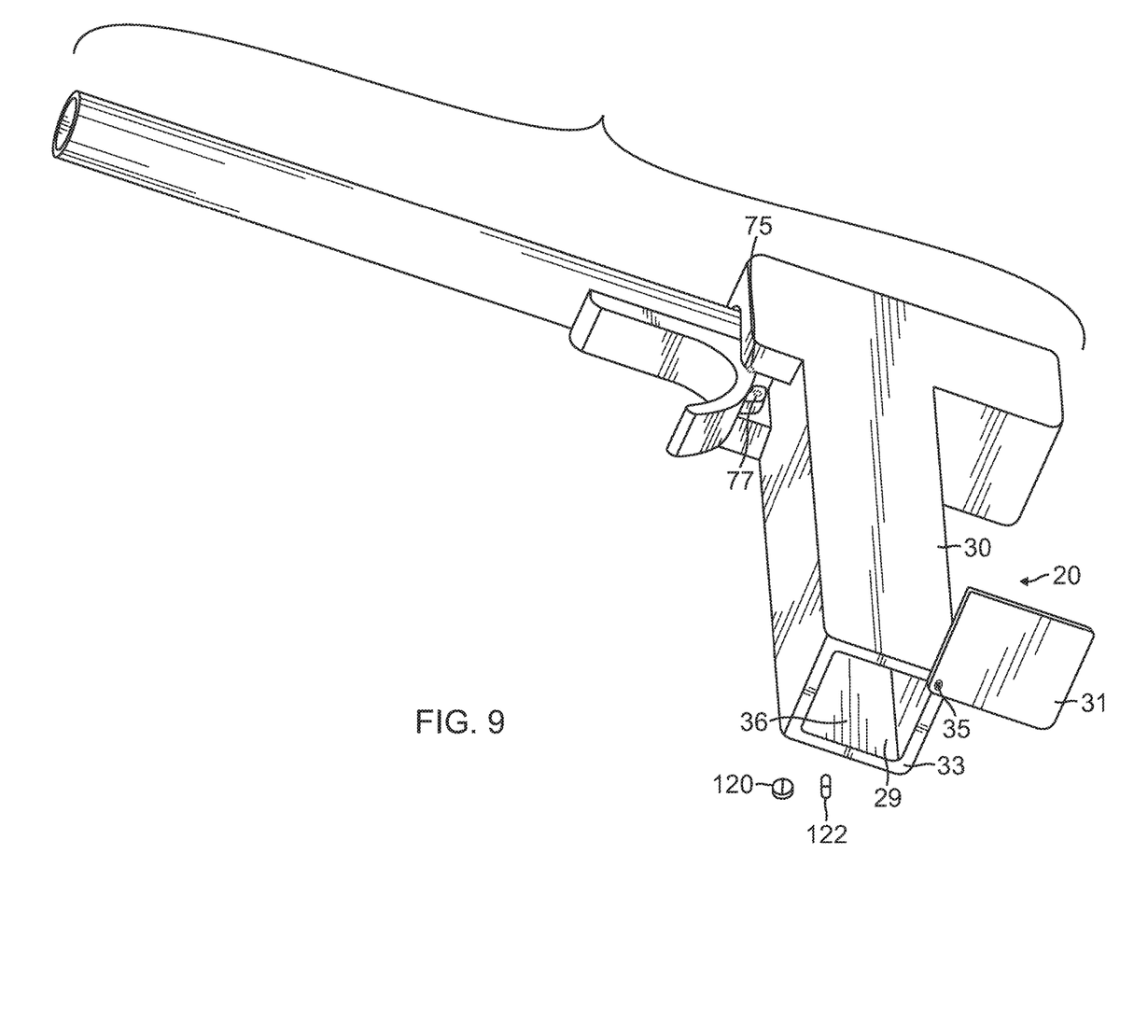
FIG. 9 is a bottom perspective view of the present invention solid animal medicine administrator illustrating a closing member rotated away from the bottom to expose a pill and capsule retaining chamber within the handle.

Referring to FIG. 9, the grip section 30 of handle 20 has an interior chamber 36 in which pills and capsules are stored with a closing door 31 rotatably affixed to the bottom wall 33 of grip section 30 by rotating means such as pin 35. The closing door 31 is rotated away from the bottom opening 29 of chamber 36 and after pill 120 and capsule 122 are inserted into chamber 36, the closing door 31 is rotated into a closed position to prevent the pill or capsule from falling out. The closing door can also be a plug-type device which is removed and reinserted after the solid animal medicine is in the chamber.

Figure 6:
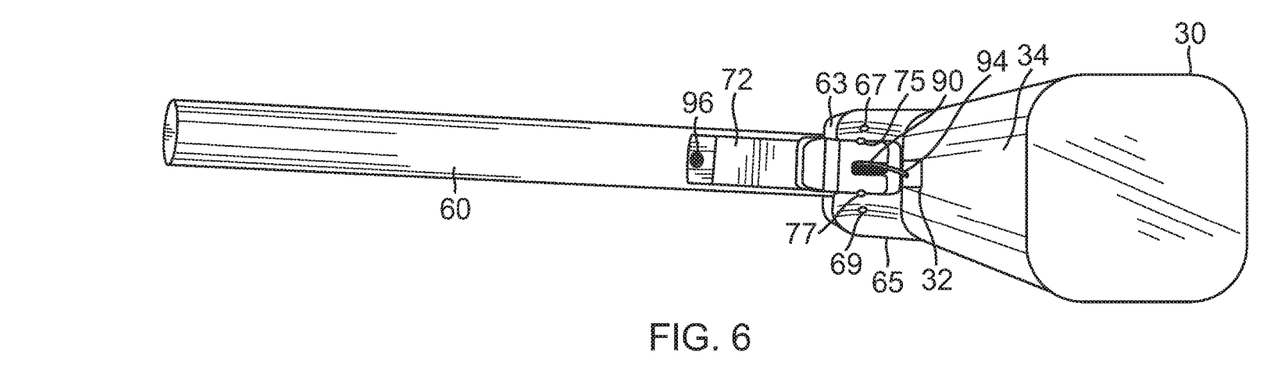
FIG. 6 is a bottom plan view of the present invention solid animal medicinal administrator with a member having a larger interior opening.
Figures 6A, 7:
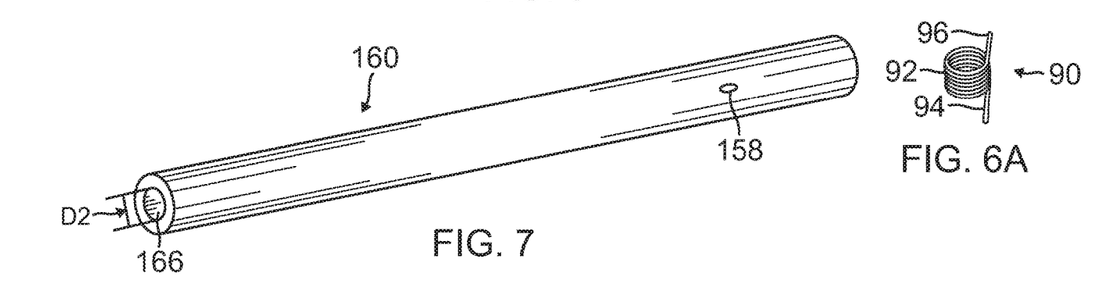
FIG. 6A is a side perspective view of the torsion spring.
FIG. 7 is a perspective view of an alternative member with a medium size interior opening.
Figure 8:
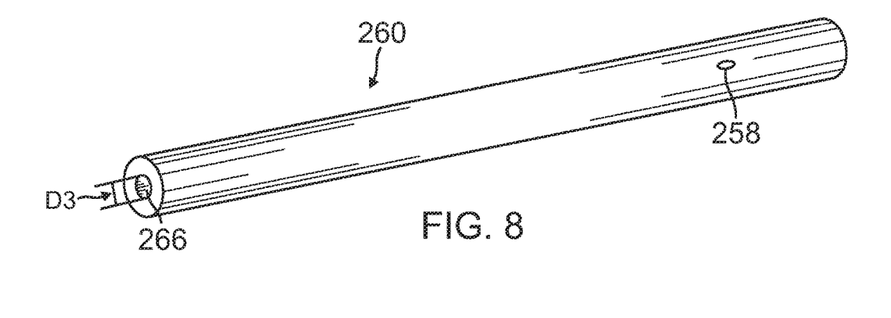
FIG. 8 is a perspective view of another alternative embodiment of the member with a small size interior opening.

Dispensing tube 60 has the largest diameter "D1" for interior chamber 58. Referring to FIG. 7, a second dispensing tube 160 with a smaller diameter "D2" for interior chamber 166 can replace dispensing tube 60. Second dispensing tube 160 has a transverse opening 158 at the same location as transverse opening 58 to receive blocking member 74. Referring to FIG. 8, a third dispensing tube 260 with the smaller diameter "D3" for interior chamber 266 can replace dispensing tubes 60 and 160. Third dispensing tube 260 has a transverse opening 258 at the same location as transverse opening 60 to receive blocking member 74. All dispensing tubes 60, 160 and 260 can be the same length and extend into transverse section 30 of handle 20 as previously described.

A spring member such as a torsion spring 90 is illustrated in FIG. 6A and has a coil 92 with a first flat member 94 and a second flat member 96. As illustrated in FIG. 6, the torsion spring 90 has a coil 92 embedded into the trigger 70 as illustrated in FIG. 6 with the first flat member 94 retained in slot 32 on interior face 34 of hand grip section 30 and the second flat member 96 embedded into the first section 72 of trigger mechanism 70.

Figure 4:
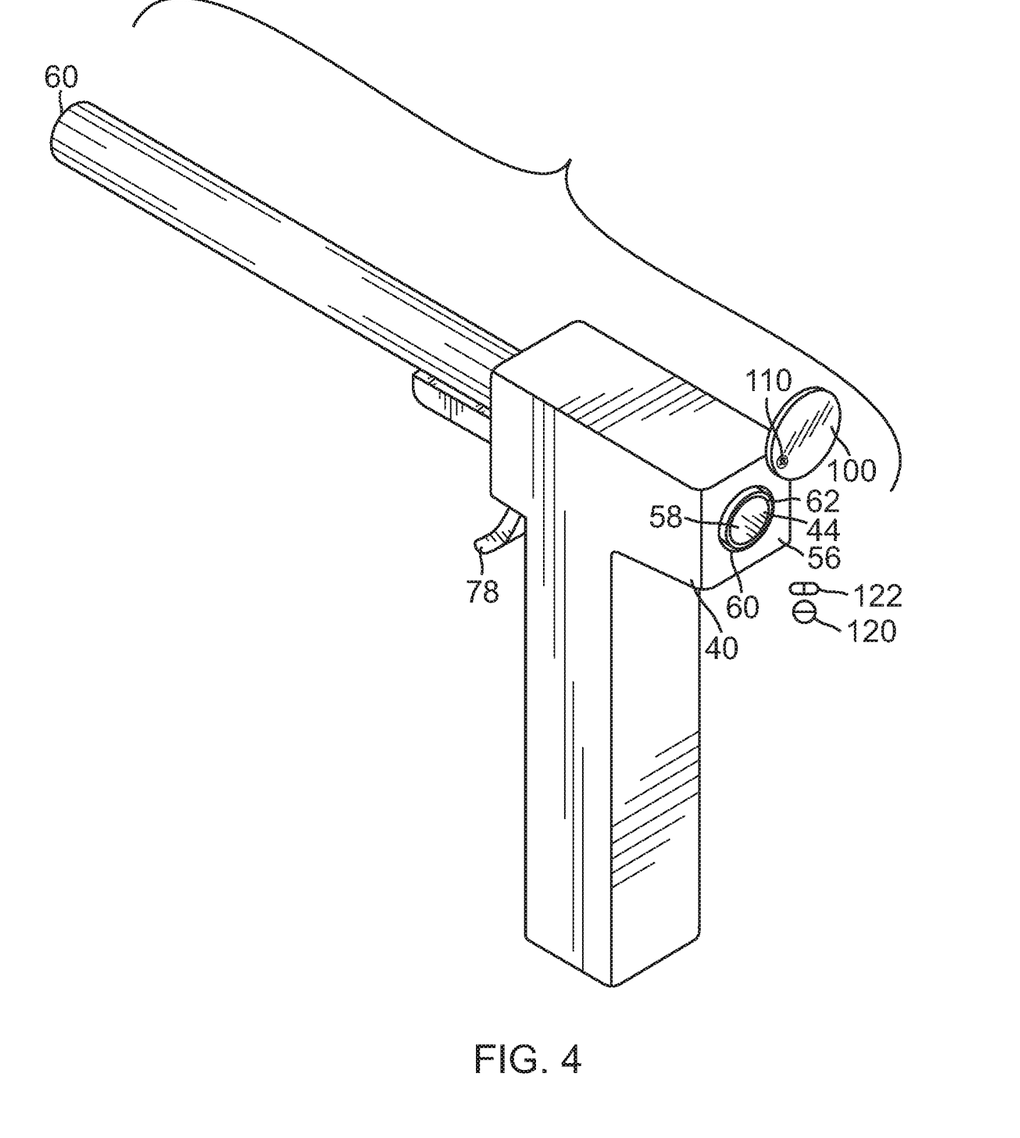
FIG. 4 is a rear perspective view of the present invention solid medicine animal administrator with the swing disc opened to insert solid animal medicine selected from the group consisting of pills and/or capsules into the administration cylinder.
Figure 5:
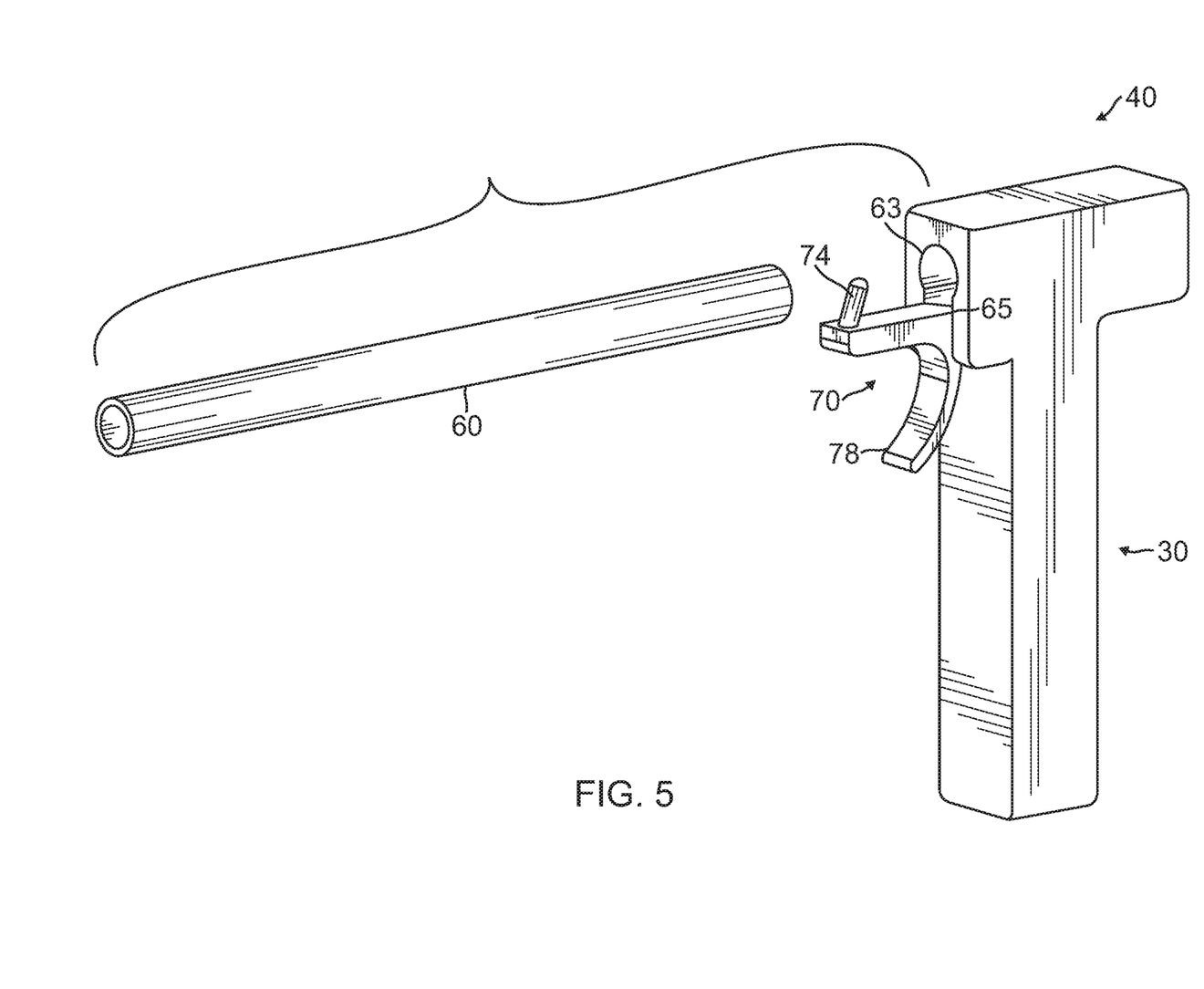
FIG. 5 is an exploded view of the present invention solid medicine animal administrator with the solid animal medicine administration member separated from the handle to better illustrate the trigger mechanism and blocking pin.

Referring to FIG. 4, the distal end 62 of the dispensing tube 60 is closed by a closing member which, by way of example, is a rotating disc 100 affixed by a rotation member 110 which is a pin which is affixed to the rear wall 56 at the distal end 44 of the transverse section 40 of handle 20. The closing member can also be a removable closing door. Pill 120 or capsule 122 is inserted into the distal end 62 of interior chamber 58 of dispensing tube 60. The rotating disc 100 is then closed and the pill 120 or capsule 122 falls through interior chamber 58 until it is stopped by the blocking member 74 which stops movement of the pill or capsule. The proximal end 66 of the dispensing tube 60 is inserted into the animal's mouth and then a hand grips the handle 20 so that a finger applies a squeezing force on the trigger section 78 of the trigger mechanism 70 to move the trigger section 78 toward the interior face 34 of hand grip section 30 to overcome the force of torsional spring 90 so that blocking member 74 rotates out of interior chamber 58 and the pill 120 or capsule 122 falls into the animal's mouth. The proximal end 66 is inserted deep enough so that pill or capsule goes into the animal's throat so the animal cannot spit it out. When the squeezing force from a finger is removed, the torsion spring 90 causes the blocking member 74 to rotate back into the hollow chamber 58 of dispensing tube 60.

Of course the present invention is not intended to be restricted to any particular form or arrangement, or any specific embodiment, or any specific use, disclosed herein, since the same may be modified in various particulars or relations without departing from the spirit or scope of the claimed invention hereinabove shown and described of which the apparatus or method shown is intended only for illustration and disclosure of an operative embodiment and not to show all of the various forms or modifications in which this invention might be embodied or operated.

What is claimed is:

1. A device to administer a solid animal medicine to an animal, comprising:

a) a handle having a hand grip section and a transverse section, the transverse section of the handle including an elongated opening having a given diameter extending from a distal end to a proximal end, the elongated opening of the transverse section of the handle retaining a first dispensing tube having a distal end aligned with the distal end of the elongated opening in the transverse section, the dispensing tube extending past the proximal end of the elongated opening in the transverse section and extending for a distance of at least several inches to a proximal end of the dispensing tube, the dispensing tube having an exterior wall with an exterior surface having a diameter which enables the dispensing tube to be press fit retained within the elongated opening of the transverse section of the handle, the dispensing tube having an interior hollow chamber surrounded by the dispensing tube exterior wall, the interior hollow chamber having a given interior diameter, the dispensing tube including a transverse opening located at a given distance from the proximal end of the transverse section of the handle, the transverse opening extending from the exterior surface of the exterior wall into the interior hollow chamber of the dispensing tube;
b) a trigger mechanism rotatably affixed to a proximal opening in the transverse section of the handle, the trigger mechanism including a first section aligned with the dispensing tube and a blocking member which extends through the transverse opening in the dispensing tube and into the hollow interior chamber of the dispensing tube, the blocking member extending from an interior surface of the hollow chamber at the transverse opening to adjacent an interior surface of the hollow chamber at a location at an opposite end of the interior diameter of the dispensing tube, the trigger mechanism being affixed to exterior walls of a proximal opening of the hand grip section of the handle with a rotation member supported by a head of the trigger mechanism, the head of the trigger mechanism extending to a trigger section of the trigger mechanism;
c) the hand grip section of the handle having an interior chamber into in which the solid animal medicine selected from the group consisting of pills and capsules are configured to be stored with a closing door removably affixed to a bottom wall of the hand grip section;
d) a spring member embedded into the trigger mechanism and partially retained in a slot on an interior surface of a hand grip section and partially retained in a first section of the trigger mechanism; and
e) the distal end of the dispensing tube being closed by a closing member rotatably affixed to a rear wall at the distal end of the transverse section of the handle, wherein the solid animal medicine can be inserted into the distal end of the interior chamber of dispensing tube when the closing member is in an open condition, wherein the closing member is configured to be rotated to a closed position after the solid animal medicine has been inserted into the interior chamber of the dispensing tube, wherein the solid animal medicine can travel within the interior chamber of the dispensing tube until further travel is stopped by the blocking member;
whereby the device is configured such that the proximal end of the dispensing tube is configured to be inserted into a restrained animal's mouth to a location adjacent an animal's throat and the hand grip section of the handle is configured to be gripped by a user's hand so that at least one finger of the user's hand can apply a squeezing force on the trigger section of the trigger mechanism to move the trigger section toward the interior face of the hand grip section to overcome the force of the spring member to thereby cause the blocking member to rotate out of the interior chamber of the dispensing tube to cause the solid animal medicine to travel to a proximal end of the dispensing tube and out of the proximal end of the interior chamber of the dispensing tube and down the animal's throat and wherein when the squeezing force from the at least one finger is removed, the spring is configured to cause the blocking member to rotate back into the hollow chamber of the dispensing tube.

2. The device to administer a solid animal medicine to an animal in accordance with claim 1, further comprising: the blocking member having an arcuate shape.

3. The device to administer a solid animal medicine to an animal in accordance with claim 1, further comprising: the blocking member being formed at an angle relative to the interior surface of the dispensing tube.

4. The device to administer a solid animal medicine to an animal in accordance with claim 1, further comprising:
   a) a multiplicity of different dispensing tubes;
   b) wherein the first dispensing tube is replaceable with any of the multiplicity of different dispensing tubes and each of the multiplicity of different dispensing tubes have a same outer diameter such that the multiplicity of different dispensing tubes are configured to be press fit into the elongated opening in the transverse section of the handle;
   c) wherein each of the multiplicity of different dispensing tubes have a different diameter of a respective interior chamber; and
   d) wherein a transverse opening in each of the multiplicity of different dispensing tubes is configured to be in the same location relative to the proximal end of the transverse section of the handle section when press fit into the elongated opening in the transverse section of the handle section.

5. The device to administer a solid animal medicine to an animal in accordance with claim 1, further comprising:
   the spring member being a torsion spring with a coil embedded within the trigger mechanism having a first flat section retained on the interior surface of the hand grip section and a second flat section retained in the first section of the trigger mechanism.

* * * * *